US009034381B2

United States Patent
Mooney et al.

(10) Patent No.: US 9,034,381 B2
(45) Date of Patent: May 19, 2015

(54) PROCESS TO CONTROL PARTICLE SIZE

(75) Inventors: Brett Antony Mooney, Mt. Ommaney (AU); Panagiotis (Peter) Keramidas, Carindale (AU)

(73) Assignee: Alphapharm Pty Ltd, Carole Park (AU)

( * ) Notice: Subject to any disclaimer, the term of this patent is extended or adjusted under 35 U.S.C. 154(b) by 1054 days.

(21) Appl. No.: 12/093,045

(22) PCT Filed: Nov. 10, 2006

(86) PCT No.: PCT/AU2006/001687
§ 371 (c)(1),
(2), (4) Date: Aug. 8, 2008

(87) PCT Pub. No.: WO2007/053904
PCT Pub. Date: May 18, 2007

(65) Prior Publication Data
US 2009/0220609 A1 Sep. 3, 2009

(30) Foreign Application Priority Data
Nov. 10, 2005 (AU) ................................ 2005906227

(51) Int. Cl.
A61K 9/14 (2006.01)
(52) U.S. Cl.
CPC ........................................ A61K 9/14 (2013.01)
(58) Field of Classification Search
None
See application file for complete search history.

(56) References Cited

U.S. PATENT DOCUMENTS

| RE37,516 E | 1/2002 | Grebow et al. | |
| 6,383,520 B1 * | 5/2002 | Hirayama et al. | 424/489 |
| 2002/0022056 A1 * | 2/2002 | Schlutermann | 424/489 |
| 2002/0035119 A1 | 3/2002 | Kumar et al. | |
| 2003/0175338 A1 | 9/2003 | Singh et al. | |
| 2004/0118007 A1 | 6/2004 | Chickering, III et al. | |

(Continued)

FOREIGN PATENT DOCUMENTS

| EP | 1 336 405 A1 | 8/2003 |
| EP | 1951197 A1 | 8/2008 |
| WO | 98/35681 A1 | 8/1998 |

(Continued)

OTHER PUBLICATIONS

M. Dimirel, et al, Formulation and in vitro-in vivo evaluation of piribedil solid lipid micro- and nanoparticles, J. Microencapsulation, 2001, vol. 18, No. 3, pp. 359-369.

(Continued)

*Primary Examiner* — Anand Desai
*Assistant Examiner* — Melissa Mercier

(57) ABSTRACT

A multi-stage process to control the particle size of a pharmaceutical substance comprising the steps of: passing the pharmaceutical substance through a first stage of a particle size reduction process with a first set of particle size control parameters to obtain a feedstock of reduced median particle size and lesser distribution of median particle size for a second stage of a particle size reduction process; passing the feedstock, through a second stage of a particle size reduction process with a second set of particle size control parameters; optionally, using the product of the second stage or subsequent stages as a feedstock in further stages of a multi-stage particle size reduction process with a set of particle size control parameters for each stage; and collecting a pharmaceutical substance with a median particle size greater than 10 μm and with a narrow, reproducible distribution of median particle sizes.

27 Claims, 1 Drawing Sheet

(56) References Cited

U.S. PATENT DOCUMENTS

| | | | |
|---|---|---|---|
| 2005/0079138 A1* | 4/2005 | Chickering et al. | 424/46 |
| 2005/0145729 A1* | 7/2005 | Stachowski et al. | 241/27 |

FOREIGN PATENT DOCUMENTS

| | | |
|---|---|---|
| WO | 03080056 A2 | 1/2003 |
| WO | 03082241 A2 | 10/2003 |
| WO | WO2006030301 A1 | 3/2006 |
| WO | WO2007053904 A1 | 5/2007 |

OTHER PUBLICATIONS

J.P. Guichard, et al., A New Formulation of Fenofibrate: Suprabioavailable Tablets, Current Medical Research and Opinion®, vol. 16, No. 2, 2000, pp. 134-138.

David B. Miller, et al., Clinical Pharmacokinetics of Fibric Acid Derivatives (Fibrates), Clin Pharmacokinet Feb. 1998; 34 (2): pp. 155-162.

Norbert Rasenack and Bernd W. Müller, Ph.D, Micron-Size Drug Particles: Common and Novel Micronization Techniques,.Pharmaceutical Development and Technology, vol. 9, No. 1, 2004; pp. 1-8.

A.S. Ridolfo, et al, Benoxaprofen, a New Anti-Inflammatory Agent: Particle-Size Effect on Dissolution Rate and Oral Absorption in Humans, Journal of Pharmaceutical Sciences, vol. 68, No. 7, Jul. 1979; 850-852.

R.D. Schoenwald and P. Stewart, Effect of Particle Size on Ophthalmic Bioavailability of Dexamethasone Suspensions in Rabbits, Journal of Pharmaceutical Sciences, vol. 69, No. 4, Apr. 1980, 391-394.

Shastri, Ph.D., Relationship Among Particle Size Distribution, Dissolution Profile, Plasma Values, and Anthelmintic Efficacy of Oxfendazole, American Journal Vet Res, vol. 41, No. 12, Dec. 1990; pp. 2095-2101.

J.J.A.M. Verheezen et al, Milling of agglomerates in an impact mill, International Journal of Pharmaceutics 278, (Mar. 2004) 165-172.

R.L. Wolen, et al., The Effect of Crystal Size on the Bioavailability of Benoxaprofen: Studies Utilizing Deuterium Labeled DrugBiomedical Mass Spectroetry, vol. 6, No. 4, 1979; pp. 173-178.

Ezerskii, M.L., et al., "Use of a Jet Mill to Obtain Powders of Pharmaceutical Preparations", Pharmaceutical Chemistry Journal, vol. 6, pp. 681-684 (1972).

Austalian Government—IP Australia, Examiner's first report on patent application No. 2006313009, Jan. 31, 2012.

European Patent Office, Extended European Search Report for European Application No./Patent No. 06804507.9-1219 / 1951197 PCT AU2006001687 dated Nov. 23, 2011.

Demirel, M., et al., Formulation and in vitro-in vivo evaluation of piribedil solid lipid micro- and nanoparticles, J. Microencapsulation, 2001, pp. 359-371, vol. 18, No. 3.

Rasenack, N., et al., Micron-Size Drug Particles: Common and Novel Micronization Techniques, Pharmaceutical Development and Technology, 2004, pp. 1-13, vol. 9, No. 1.

Shastri, S., Ph.D., et al., Relationship Among Particle Size Distribution, Dissolution Profile, Plasma Values, and Anthelmintic Efficacy of Oxfendazole, American Journal of Veterinary Research, Dec. 1980, pp. 2095-2101, vol. 41, No. 12.

Wolen, R.L., et al., The Effect of Crystal Size on the Bioavailability of Benoxaprofen: Studies Utilizing Deuterium Labeled Drug, Biomedical Mass Spectrometry, 1979, pp. 173-178, vol. 6, No. 4.

* cited by examiner

PROCESS TO CONTROL PARTICLE SIZE

TECHNICAL FIELD

A process for the production of a pharmaceutically active substance with a tightly controlled, reproducible distribution of median particle size, particles of a pharmaceutically active substance with a tightly controlled, reproducible distribution of median particle size and a pharmaceutical composition containing a pharmaceutically active substance with a tightly controlled, reproducible distribution of median particle size.

BACKGROUND ART

Pharmaceutically active substances are commonly formulated into dosage forms to aid the delivery of small amounts thereof. The amount of pharmaceutically active substance that will be present in the dosage form can vary from a very small amount such as about 0.5 mg up to larger amounts such as about 1000 mg, depending on the pharmaceutically active substance and the pharmaceutical effective amount thereof. In order to be able to accurately administer these amounts of pharmaceutically active substance, the dosage form often includes pharmaceutical acceptable excipients that perform various functions depending on the dosage form and the mode of action required. These excipients have an effect on the method and rate of delivery of the pharmaceutically active substance to the patient.

Another aspect of pharmaceutical formulations that affects the rate of delivery or the bioavailability of the pharmaceutically active substance is the particle size. This relationship between particle size and bioavailability is well known in the pharmaceutical industry and across a range of pharmaceutical products. In 1979, studies into the effect of crystal size on the bioavailability of Benoxaprofen were conducted (Biomed Mass Spectrom., 1979 April, 6(4), pp 173-8, Wolen R L et al; J. Pharm. Sci., 1979 July, 68(7), pp 850-2, Ridolfo A S et al). J. Pharm. Sci., 1980 April, 69(4), pp 391-4, Schoenwald R D & Stewart P disclose the effect of particle size on the ophthalmic bioavailability of dexamethasone stating that "A statistically significant rank-order correlation was observed between increasing drug levels and decreasing particle size." Other examples include American Journal of Veterinary Research, 1980 December, 41(12), pp 2095-2101, Shastri S et al; Clinical Pharmacokinetics, 1998 February, 34(2), pp 155-62, Miller D B & Spence J D; Current Med Res Opin, 2000, 16(2), pp 134-8, Guichard J P et al; J. Microencapsul., 2001 May-June, 18(3), pp 359-71, Demirel M et al; and Pharmaceutical Dev Technol, 2004, 9(1), pp 1-13, Rasenick N & Muller B W. Also refer to US 2002035119 A1 Rajiv, M et al; US 2003175338 A1 Manoj, K P et al; WO 03/082241 A3 Kumar, P M et al; WO 03/080056 A2 Teva Pharmaceutical Industries Ltd; and US RE37516 E Grebow, P E et al that discuss the relationship between particle size and bioavailability of the pharmaceutically active substance.

Bioavailability can also be increased with the use of a surfactant or wetting agent. This helps to increase the solubility of the pharmaceutically active substance and thus bioavailability. However, there can be an undesired interaction between the pharmaceutically active substance and the wetting agent. Therefore, it is not always beneficial to use a wetting agent to increase the solubility and/or bioavailability of a pharmaceutically active substance.

Particle sizes of substances can be measured using various commonly available methods such as measurement using light (eg. light-scattering methods or turbidimetric methods), sedimentation methods (eg. pipette analysis using an Andreassen pipette, sedimentation scales, photosedimentometers or sedimentation in a centrifugal force), pulse methods (eg. Coulter counter), or sorting by means of gravitational or centrifugal force.

There are various known methods for the control of the particle size of substances including reduction by comminution or de-agglomeration by milling and/or sieving, or particle size increase by agglomeration through granulation, blending or a mixture thereof. These methods use commonly available equipment and/or methods for the reduction or increase of the particle sizes of material. However, these techniques do not allow for the production of a substance with a very narrow, reproducible and consistent distribution of particle size without the need to reprocess, rework or destroy those particles outside of the required distribution. Thus, these processes can be time consuming and costly if reworking of the material under the desired size is not able to be performed. In those circumstances, it is common for the fine material to be destroyed or reprocessed.

Spray-drying can also be used to achieve particles in a narrow particle size distribution. However, inconsistency of the particle size of the feedstock for this process can cause problems with the apparatus such as blockage of the spray jets.

Multi-stage milling techniques have been used on a limited basis in the past to provide substances, such as those for use in inhalants and steroids, where the median particle size is extremely low, eg. below 5 μm, with steep cut-offs on both ends of the particle size spectrum. These processes have required a step-down reduction of particles from >100 μm to ~50 μm, then to ~20 μm and finally to below 5 μm. This last stage is not tightly controlled in that the substance with a median particle size of below 5 μm of its very nature must have a narrow distribution of particle size. However, substances with median particle sizes larger than ~10 μm but still with a narrow, reproducible and consistent distribution have not been manufactured by these techniques in the past.

Other techniques that have been used to obtain uniform particles in a narrow, reproducible and consistent distribution of particle sizes include layering the pharmaceutically active substance onto carrier particles having uniform particle size or spray-drying to form particles of uniform size distribution. Layering or coating requires further processing in specialised equipment designed for small particles and carrier particles in the size distribution required are not always commercially available. Spray-drying techniques also require specialised equipment and it may not be possible to put the pharmaceutically active substance being handled into a solution to be spray-dried. Otherwise the solvent necessary to dissolve the pharmaceutically active substance may not be available or it may not be acceptable for pharmaceutical use. This can be because the pharmaceutically active substance is not stable in solution and degrades or because the solvent is not totally removed from the final product and its residual presence would be unacceptable to health authorities, thereby making the pharmaceutically active substance, and its resultant pharmaceutical product, unacceptable for registration or administration.

Extrusion and spheronising are combined techniques that can give particles with a uniform size and a narrow, reproducible and consistent distribution of particle size. This combined technique requires the pharmaceutically active substance to be made into a paste-like form that can be extruded. The limitation of this technique is that it is difficult to achieve the production of small particles below 200 μm and is generally used for particles above 0.3 mm (300 μm).

SUMMARY OF INVENTION

We have surprisingly found that a narrow, reproducible and consistent distribution of median particle size for particles of a pharmaceutically active substance can be achieved by using a multi-stage reduction process without the necessity to reprocess, reject or destroy large quantities of particles outside of the desired range.

In a first aspect the present invention provides a multi-stage process to control the particle size of a pharmaceutical substance comprising the steps of:

passing the pharmaceutical substance through a first stage of a particle size reduction process with a first set of particle size control parameters to obtain a feedstock of reduced median particle size and lesser distribution of median particle size for a second stage of a particle size reduction process;

passing the feedstock, through a second stage of a particle size reduction process with a second set of particle size control parameters;

optionally, using the product of the second stage or subsequent stages as a feedstock in further stages of a multi-stage particle size reduction process with a set of particle size control parameters for each stage; and collecting a pharmaceutical substance with a median particle size greater than 10 μm and with a narrow, reproducible distribution of median particle sizes.

In an embodiment the particle size reduction process is a milling process.

In an embodiment the particle size reduction process is selected from the group consisting of jet milling, hammer milling, compression milling and tumble milling processes, most particularly a jet milling process. Particle size control parameters for these processes are well understood by the person skilled in the art. For example the particle size reduction achieved in a jet milling process is controlled by adjusting a number of parameters, the chief ones being mill pressure and feed rate. In a hammer mill process, the particle size reduction is controlled by the feed rate, the hammer speed and the size of the opening in the grate/screen at the outlet. In a compression mill process, the particle size reduction is controlled by the feed rate and amount of compression imparted to the material (e.g. the amount of force applied to compression rollers).

In a second aspect the invention provides a pharmaceutical substance manufactured by a process as described herein.

In a third aspect the invention provides a pharmaceutical composition containing a pharmaceutical substance wherein at least 50% of the particles have a particle size deviating no more than between 1 μm and 10 μm from the median particle size, and at least one other pharmaceutically acceptable ingredient.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It will be clearly understood that, although a number of prior art publications are referred to herein, this reference does not constitute an admission that any of these documents forms part of the common general knowledge in the art, in Australia or in any other country.

BRIEF DESCRIPTION OF THE DRAWINGS

Preferred embodiments of the invention will now be described with reference to the accompanying drawings, in which.

DETAILED DESCRIPTION OF PREFERRED EMBODIMENTS

Figure 1:
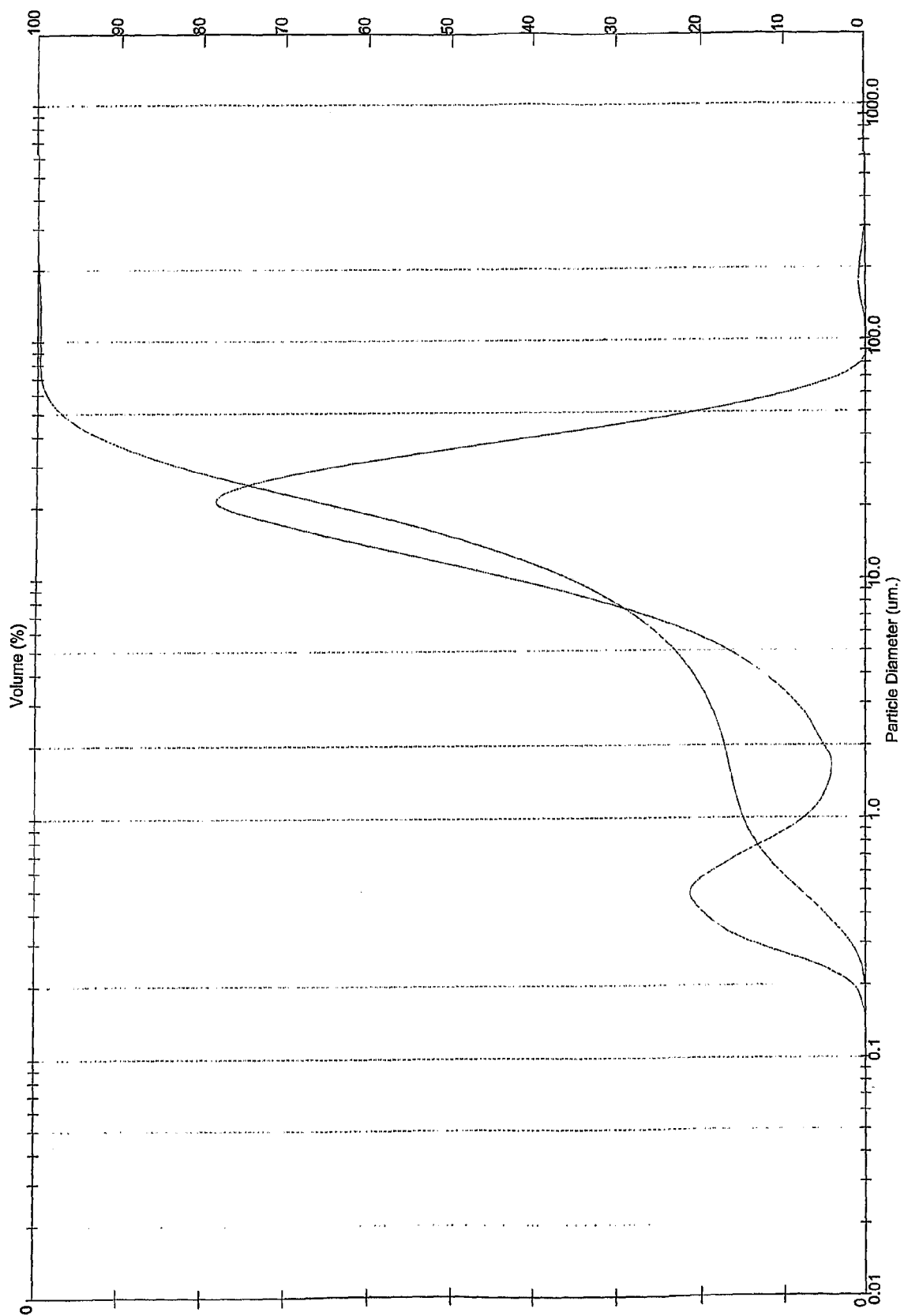
FIG. 1 is graph showing the particle diameter distribution on the left hand axis, cumulative volume on the right hand axis vs particle diameter (μm) for an average of all of the separate samples set forth in Table 5.

The stepwise reduction of material can produce a median particle size of greater than 10 μm, for example between 10 μm and 50 μm, more preferably between 10 μm and 20 μm, with at least 50% of the particles having a median particle size distribution of about 1 μm to 10 μm. Put another way, in an embodiment at least 50% of the particles have a particle size deviating no more than between 1 μm and 10 μm from the median particle size. In further embodiments this may 1 μm to 5 μm or even 1 μm to 3 μm. In order to get material with a median particle size of greater than 10 μm with a narrow, reproducible and consistent distribution, the feedstock going into the final reduction process needs to be such that it does not have a large range of particle sizes. Therefore, the particle size of the feedstock entering into the final reduction process needs to be controlled but to a lesser extent than the desired final product. In order to achieve this, the material is sequentially reduced in a series of milling processes whereby the distribution of particle sizes is gradually tightened. The reduction of material with a wide distribution of particle sizes in a single process will afford a material with reduced median particle size but still with a wide distribution of particle sizes and a product whose median particle size is not uniform from one batch to the next.

The process of the invention involves taking the feedstock of material with a larger median particle size and a larger distribution of particle sizes than that required in the final product and reducing the median particle size and the distribution of particle sizes in a step-wise manner. The stepped process takes a feedstock with a large median particle size that has a large distribution and reduces it such that the median particle size decreases and, more importantly, the distribution of particle size becomes narrower. This is then used as the feedstock for the next reduction stage. This can be continued until material with the desired median particle size and distribution have been achieved.

Whilst not wishing to be contained to a specific hypothesis of how this is achieved, it is understood that the reduction process requires energy to be imparted into the material. The larger the starting material, the more energy that is required to reduce it and vice-versa with regard to smaller particles. There comes a time when no more energy can be efficiently imparted into a material in a single process to achieve large reductions and the application of a large amount of energy to the smaller particles reduces their size dramatically causing a large spread in the particle size distribution. Therefore, a starting feedstock that has a wide distribution of particle sizes will yield a reduced material still with a wide particle size distribution because the same amount of energy has been imparted to all of the particles regardless of their size. Thus, it is believed that a multi-stage reduction process alleviates this problem by sequentially imparting smaller amounts of energy in multiple reduction processes rather than trying to impart all of the energy into the material in one reduction process.

The process of the invention is applicable to any pharmaceutical substance where there is a need to tightly control the particle size of the substance. The pharmaceutical substance can be chosen from pharmaceutically active substances and/or from pharmaceutically acceptable excipients. The pharmaceutically active substance may be selected from anti-depressant agents such as paroxetine, fluoxetine, sertraline, citalopram, escitalopram, venlafaxine, desvenlafaxine and mirtazapine, anti-epileptic agents such as carbamazepine, oxcarbazepine, gabapentin, pregabalin and tiagabine, antihypertensive agents such as ramipril, quinapril, enalapril, perindopril, trandolapril, captopril, lisinopril, oxeprenolol, nifedipine, atenolol, verapamil, hydralazine, pindolol, metoprolol, carvedilol, bisoprolol, diltiazem, frusemide and propranolol, proton pump inhibitors such as omeprazole, lansoprazole, esomeprazole, rabeprazole and pantoprazole, angiotensin type II receptor antagonists such as candesartan, eprosartan, irbesartan, losartan, telmisartan and valsartan, anti-diabetic agents such as repaglinide and the glitazones (troglitazone, ciglitazone, pioglitazone and rosiglitazone), sitagliptin, vildagliptin, saxagliptin, NVP DPP728, P32/98, FE 999011, PHX1149, anti-schizophrenic agents such as aripiprazole, thioridazine, chlorpromazine, clozapine, zuclopenthixol, flupenthixol, droperidol, haloperidol, risperidine, quetiapine, amisulpride and olanzapine agents for treating ADHD such as methylphenidiate and atomoxetine, and anti-cholesteremia agents such as gemfibrozil, colestipol, ezetemibe, fluvastatin, simvastatin, fenofibrate, atorvastatin and pravastatin, malarial treatment agents such atovaquone and proguanil or pharmaceutically acceptable salts thereof.

The pharmaceutical substance can be selected from pharmaceutically acceptable excipients such as talc, lactose, polyvinylpyrrolidone, cellulosic derivatives such as hydroxyethyl cellulose, hydroxypropyl cellulose, hydroxypropyl methylcellulose and sodium carboxymethyl cellulose.

In a preferred embodiment, the invention provides a process for the production of a pharmaceutical composition comprising the inclusion of a pharmaceutical substance with a median particle size of between 10 μm and 50 μm, with at least 50% of the particles having a median particle size distribution of 1 μm to 10 μm, into a pharmaceutical dosage form. The dosage form can be selected from tablet, capsule, inhaler, injectable, suppository, solution or syrup or the like. The dosage form will optionally comprise other excipients and may also be film coated for cosmetic and/or controlled rate release purposes, as are well known to those skilled in the art of pharmaceutical formulation.

It has been found that material used in a suspension layering spraying process is best if it has a very narrow particle size distribution, such as manufactured by the process of this invention. This is because the material with a uniform particle size gives uniform loading of the substance onto the carrier particles and gives a uniform suspension that will not easily segregate or settle out. It also has the added benefit of reducing machine down time and equipment maintenance, as uniform particle size has been shown to reduce blockage of the spray jet nozzles of the spray apparatus.

Example 1 (Comparative)

Oxcarbazepine was milled to obtain a target $D_{[v,0.5]}$ of between 12 μm to 15 μm. The median particle size ($D_{[v,0.5]}$) of the feedstock was 47.41 μm with a $D_{[v,0.9]}$ of 100.29 μm. This was milled in a single process and produced material with an average $D_{[v,0.5]}$ of 15.27 μm with a distribution of $D_{[v,0.5]}$ of 10.36 μm to 25.41 μm and an average $D_{[v,0.9]}$ of 53.30 μm with a distribution of $D_{[v,0.9]}$ of 44.13 μm to 67.97 μm.

TABLE 1

Particle Size Results

| Stage | Sample | $D_{[v,0.5]}$ μm | $D_{[v,0.9]}$ μm |
|---|---|---|---|
| Feedstock | 1 | 47.04 | 98.61 |
|  | 2 | 47.77 | 101.96 |
|  | Mean | 47.41 | 100.29 |
| Micronised | Sample 1 | 25.41 | 67.97 |
|  | Sample 2 | 10.36 | 44.13 |
|  | Sample 3 | 15.02 | 52.08 |
|  | Sample 4 | 15.18 | 51.71 |
|  | Sample 5 | 15.16 | 51.94 |
|  | Composite | 15.27 | 53.30 |

Example 2 (Comparative)

Oxcarbazepine was milled to obtain a target $D_{[v,0.5]}$ of less than 10 μm. The $D_{[v,0.5]}$ of the feedstock was 47.41 μm with a $D_{[v,0.9]}$ of 100.29 μm. This was milled in a single process and produced material with an average $D_{[v,0.5]}$ of 5.95 μm with a distribution of $D_{[v,0.5]}$ of 2.15 μm to 6.09 μm and an average $D_{[v,0.9]}$ of 30.47 μm with a distribution of $D_{[v,0.9]}$ of 11.56 μm to 31.90 μm.

TABLE 2

Particle Size Results

| Stage | Sample | $D_{[v,0.5]}$ μm | $D_{[v,0.9]}$ μm |
|---|---|---|---|
| Feedstock | 1 | 47.04 | 98.61 |
|  | 2 | 47.77 | 101.96 |
|  | Mean | 47.41 | 100.29 |
| Micronised | Sample 1 | 2.15 | 11.56 |
|  | Sample 2 | 4.91 | 27.25 |
|  | Sample 3 | 3.84 | 19.56 |
|  | Sample 4 | 6.09 | 31.90 |
|  | Composite | 5.95 | 30.47 |

Example 3 (Comparative)

Oxcarbazepine was milled to obtain a target $D_{[v,0.5]}$ of between 13 μm to 17 μm. The $D_{[v,0.5]}$ of the feedstock was 73.33 μm with a $D_{[v,0.9]}$ of 323.50 μm. This was milled in a single process and produced material with a $D_{[v,0.5]}$ of 13.79 μm with a distribution of $D_{[v,0.5]}$ of 7.50 μm to 19.51 μm and an average $D_{[v,0.9]}$ of 33.14 μm with a distribution of $D_{[v,0.9]}$ of 16.47 μm to 44.34 μm.

TABLE 3

Particle Size Results

| Stage | Sample | $D_{[v,0.5]}$ μm | $D_{[v,0.9]}$ μm |
|---|---|---|---|
| Feedstock | Feed | 73.33 | 323.50 |
| Micronised | Sample 1 | 7.50 | 16.47 |
|  | Sample 2 | 19.51 | 44.34 |
|  | Sample 3 | 15.09 | 34.47 |
|  | Sample 4 | 15.64 | 35.78 |
|  | Composite | 13.79 | 33.14 |

Example 4

Oxcarbazepine was milled in a 12" spiral jet mill to produce a target $D_{[v,0.5]}$ of 15 μm to 17 μm. The $D_{[v,0.5]}$ of the initial feedstock was 65.06 μm with a range between 61.51 μm and 69.35 μm and with a $D_{[v,0.9]}$ of 177.81 μm with a range between 168.78 μm and 191.19 μm. This was milled to produce material with an average $D_{[v,0.5]}$ of 33.89 μm, distribution of 29.77 μm to 37.95 μm and having an average $D_{[v,0.9]}$ of 78.22 μm, distribution of 67.66 μm to 90.19 μm. This was then further milled to produce the desired material with a $D_{[v,0.5]}$ of 16.30 μm, distribution of 14.67 μm to 17.29 μm with a $D_{[v,0.9]}$ of 37.22 μm, distribution of 33.12 μm to 39.31 μm. The particle size control parameters were set for the first pass, and then re-set when the product of that pass was used as the feedstock for a second pass, as set forth in Table 4.

TABLE 4

Air Jet Milling Parameters

|  | Pass 1 | Pass 2 |
|---|---|---|
| Mill pressure (psi) | 5 | 14 |
| Venturi pressure (psi) | 15 | 15 |
| Feed rate (kg/hr) | 10 | 11 |

The resultant material was collected in 5 drums. Each drum was sampled at the top, middle and bottom and the $D_{[v,0.5]}$ μm (or median particle size) and the $D_{[v,0.9]}$ determined for each sample as set forth in Table 5 for each stage of the process. These samples all show a tight particle size distribution following the second pass. Particle size measurements were made using a Malvern Mastersizer S laser diffraction instrument operated according to standard operating procedure. The data is presented graphically in FIG. 1.

TABLE 5

Particle Size Results

| Stage | Sample | $D_{[v, 0.5]}$ | $D_{[v, 0.9]}$ |
|---|---|---|---|
| Feedstock | Top | 65.54 | 187.36 |
|  | Top | 66.55 | 180.14 |
|  | Top | 64.82 | 174.50 |
|  | Top | 63.90 | 173.62 |
|  | Top | 63.65 | 174.94 |
|  | Middle | 66.51 | 179.80 |
|  | Middle | 69.08 | 187.62 |
|  | Middle | 65.86 | 180.63 |
|  | Middle | 63.67 | 178.16 |
|  | Middle | 63.12 | 170.57 |
|  | Bottom | 65.81 | 175.42 |
|  | Bottom | 69.35 | 191.19 |
|  | Bottom | 63.88 | 174.57 |
|  | Bottom | 61.51 | 168.78 |
|  | Bottom | 62.66 | 169.87 |
|  | Mean | 65.06 | 177.81 |
| Micronised First Pass | Top | 34.91 | 77.21 |
|  | Top | 35.28 | 81.28 |
|  | Top | 33.12 | 74.85 |
|  | Top | 32.80 | 76.10 |
|  | Top | 34.94 | 85.01 |
|  | Middle | 35.86 | 77.29 |
|  | Middle | 35.44 | 81.80 |
|  | Middle | 34.86 | 82.63 |
|  | Middle | 29.77 | 67.97 |
|  | Middle | 32.80 | 76.31 |
|  | Bottom | 30.65 | 67.66 |
|  | Bottom | 37.95 | 90.19 |
|  | Bottom | 34.09 | 79.61 |
|  | Bottom | 32.94 | 77.39 |
|  | Bottom | 32.93 | 77.93 |
|  | Mean | 33.89 | 78.22 |
| Micronised Second Pass | Top | 14.67 | 33.12 |
|  | Top | 16.39 | 38.50 |
|  | Top | 16.77 | 39.31 |
|  | Top | 16.19 | 36.58 |

TABLE 5-continued

Particle Size Results

| Stage | Sample | $D_{[v, 0.5]}$ | $D_{[v, 0.9]}$ |
|---|---|---|---|
|  | Top | 15.24 | 35.04 |
|  | Middle | 16.02 | 35.92 |
|  | Middle | 17.29 | 38.96 |
|  | Middle | 16.11 | 37.92 |
|  | Middle | 16.88 | 37.48 |
|  | Middle | 15.18 | 34.03 |
|  | Bottom | 16.96 | 38.94 |
|  | Bottom | 16.90 | 38.85 |
|  | Bottom | 16.87 | 38.73 |
|  | Bottom | 16.47 | 37.14 |
|  | Bottom | 16.49 | 37.73 |
|  | Mean | 16.30 | 37.22 |

The invention claimed is:

1. A multi-stage process to control the particle size of a pharmaceutical substance comprising the steps of:
passing an initial feedstock of the pharmaceutical substance through a first stage of the multi-stage particle size reduction process, the first stage having a first set of particle size control parameters to obtain a further feedstock for at least a second stage of the multi-stage particle size reduction process;
passing the further feedstock through the second stage of the multi-stage particle size reduction process, the second stage having a second set of particle size control parameters to obtain a pharmaceutical substance with a reduced median particle size and narrower distribution of median particle size than the further feedstock; and
collecting the pharmaceutical substance of the final stage of the multi-stage particle size reduction process with a median particle size greater than 10 μm and with a narrow reproducible distribution of median particle size, wherein at least 50% of the particles of the pharmaceutical substance of the final stage have a particle size deviating no more than between 1 μm and 10 μm from the median particle size.

2. The process of claim 1 wherein the median particle size is between 10 μm and 50 μm.

3. The process of claim 1 wherein at least 50% of the particles have a particle size deviating no more than between 1 μm and 5 μm from the median particle size.

4. The process of claim 1 wherein at least 50% of the particles have a particle size deviating no more than between 1 μm and 3 μm from the median particle size.

5. The process of claim 1 wherein the particle size reduction process is a milling process.

6. The process of claim 5 wherein the particle size reduction process is selected from the group consisting of jet milling, hammer milling, compression milling and tumble milling processes.

7. The process of claim 6 wherein the particle size reduction process is a jet milling process.

8. The process of claim 1 wherein the pharmaceutical substance is a pharmaceutically active ingredient.

9. The process of claim 8 wherein the pharmaceutically active ingredient is selected from the group consisting of anti-depressant agents and pharmaceutically acceptable salts thereof.

10. The process of claim 9 wherein the pharmaceutically active ingredient is oxcarbazepine or a pharmaceutically acceptable salt thereof.

11. The process of claim 1 wherein the pharmaceutical substance is a pharmaceutically acceptable excipient.

12. The process of claim 11 wherein the pharmaceutically acceptable excipient is selected from the group consisting of talc, lactose, polyvinylpyrrolidone and cellulosic derivatives.

13. The process of claim 11 wherein the pharmaceutically acceptable excipient is selected from the group consisting of lactose, polyvinylpyrrolidone, hydroxyethyl cellulose, hydroxypropyl cellulose, hydroxypropyl methylcellulose and sodium carboxymethyl cellulose.

14. The process of claim 1 which is a 2 stage process.

15. The process of claim 1 which is a 3 stage process.

16. The process of claim 1 which is a 4 or more stage process.

17. A pharmaceutical substance manufactured by a process as claimed in claim 1.

18. A pharmaceutical substance with a median particle size greater than 10 µm and with a narrow reproducible distribution of median particle sizes, wherein at least 50% of the particles have a particle size deviating no more than between 1 µm and 10 µm from the median particle size.

19. The pharmaceutical substance of claim 18 wherein at least 50% of the particles have a particle size deviating no more than between 1 µm and 5 µm from the median particle size.

20. The pharmaceutical substance of claim 19 wherein at least 50% of the particles have a particle size deviating no more than between 1 µm and 3 µm from the median particle size.

21. A pharmaceutical composition containing a pharmaceutical substance manufactured by a process as claimed in claim 1, and at least one other pharmaceutically acceptable ingredient.

22. A pharmaceutical composition containing a pharmaceutical substance with a median particle size greater than 10 µm and with a narrow reproducible distribution of median particle sizes, wherein at least 50% of the particles have a particle size deviating no more than between 1 µm and 10 µm from the median particle size, and at least one other pharmaceutically acceptable ingredient.

23. A pharmaceutical composition containing a pharmaceutical substance wherein at least 50% of the particles have a particle size deviating no more than between 1 µm and 5 µm from the median particle size, and at least one other pharmaceutically acceptable ingredient.

24. A pharmaceutical composition containing a pharmaceutical substance wherein at least 50% of the particles have a particle size deviating no more than between 1 µm and 3 µm from the median particle size, and at least one other pharmaceutically acceptable ingredient.

25. The process of claim 9 wherein the pharmaceutically active ingredient is selected from the group consisting of paroxetine, fluoxetine, sertraline, citalopram, escitalopram, venlafaxine, desvenlafaxine, mirtazapine, carbamazepine oxcarbazepine, gabapentin, pregabalin, tiagabine, ramipril, quinapril, enalapril, perindopril, trandolapril, captopril, lisinopril, oxeprenolol, nifedipine, atenolol, verapamil, hydralazine, pindolol, metoprolol, carvedilol, bisoprolol, diltiazem, frusemide, propranolol, omeprazole, lansoprazole, esomeprazole, rabeprazole, pantoprazole, candesartan, eprosartan, irbesartan, losartan, telmisartan, valsartan, repaglinide, troglitazone, ciglitazone, pioglitazone, rosiglitazone, sitagliptin, vildagliptin, saxagliptin, NVP DPP728, P32/98, FE 999011, PHX1149, aripiprazole, thioridazine, chlorpromazine, clozapine, zuclopenthixol, flupenthixol, droperidol, haloperidol, risperidine, quetiapine, amisulpride, methylphenidiate, atomoxetine, gemfibrozil, colestipol, ezetemibe, fluvastatin, simvastatin, fenofibrate, atorvastatin, pravastatin, atovaquone, proguanil and pharmaceutically acceptable salts thereof.

26. The process of claim 1 wherein the multi-stage particle size reduction process comprises one or more subsequent stages each comprising the step of:
    passing the feedstock of the previous stage of the multi-stage particle size reduction process through a subsequent stage, with a set of particle size control parameters, to obtain a pharmaceutical substance with a reduced median particle size and narrower distribution of median particle size than the feedstock.

27. The process of claim 1 wherein measurements to determine the median particle size and distribution of median particle size are made using a Malvern Mastersizer S laser diffraction instrument.

* * * * *